United States Patent
Thampi et al.

(10) Patent No.: US 7,148,386 B2
(45) Date of Patent: Dec. 12, 2006

(54) PROCESSES FOR PREPARING BENZOQUINONES AND HYDROQUINONES

(75) Inventors: Jegadeesh Thampi, Karnataka (IN); Sunil Ashtekar, Bangalore (IN); Pramod Kumbhar, Mumbai (IN); Rathinam Jothi Mahalingam, Karnataka (IN)

(73) Assignee: General Electric Company, Schenectady, NY (US)

( * ) Notice: Subject to any disclaimer, the term of this patent is extended or adjusted under 35 U.S.C. 154(b) by 2 days.

(21) Appl. No.: 10/903,149

(22) Filed: Jul. 30, 2004

(65) Prior Publication Data

US 2006/0025634 A1    Feb. 2, 2006

(51) Int. Cl.
*C07C 39/10* (2006.01)
*C07C 37/00* (2006.01)
*C07C 69/96* (2006.01)

(52) U.S. Cl. .............. 568/763; 568/764; 568/771; 568/815; 558/265; 558/268

(58) Field of Classification Search ........ 568/315, 568/763, 764, 771, 815; 558/265, 268
See application file for complete search history.

(56) References Cited

U.S. PATENT DOCUMENTS

| | | | |
|---|---|---|---|
| 4,410,501 A | 10/1983 | Taramasso et al. | 423/326 |
| 4,590,305 A | 5/1986 | Drauz et al. | 568/771 |
| 5,160,496 A | 11/1992 | Constantini et al. | 568/771 |
| 5,254,746 A | 10/1993 | Costantini et al. | 568/626 |
| 5,364,982 A | 11/1994 | Brown et al. | 568/771 |
| 5,414,153 A | 5/1995 | Costantini et al. | 568/771 |
| 5,426,244 A | 6/1995 | Sugai et al. | 568/771 |
| 5,493,061 A | 2/1996 | Ratnasamy et al. | 568/771 |
| 5,756,789 A | 5/1998 | Bruce et al. | |
| 5,874,596 A | 2/1999 | Onozawa et al. | 549/531 |
| 6,133,487 A | 10/2000 | Ungarelli et al. | 568/803 |
| 6,156,939 A | 12/2000 | Vignola et al. | 568/803 |
| 6,225,436 B1 * | 5/2001 | Eiffler et al. | 528/196 |
| 6,251,851 B1 | 6/2001 | D'Amore et al. | 512/400 |
| 6,262,315 B1 | 7/2001 | Inaba et al. | 568/771 |
| 6,437,197 B1 | 8/2002 | Hamilton, Jr. | 568/802 |
| 6,441,250 B1 | 8/2002 | Atoguchi et al. | 568/771 |
| 6,479,711 B1 | 11/2002 | Takai et al. | 568/771 |
| 6,500,972 B1 | 12/2002 | Cheng et al. | 552/296 |
| 6,723,823 B1 * | 4/2004 | McCloskey et al. | 528/196 |
| 2002/0143198 A1 | 10/2002 | Cheng et al. | |

FOREIGN PATENT DOCUMENTS

EP    0 571 447    2/1992

OTHER PUBLICATIONS

Xiao, et al. "A novel catalyst of copper hydroxyphosphate with high activity in wet oxidation of aromatics" Applied Catalysis A: 207 (2001) 267-271.
Clerici, et al. "Oxidation reactions with in situ generated oxidants" Catalysis Today 41 (1998) 351-364.
Niwa, et al. "A One-Step Conversion of Benzene to Phenol with a Palladium Membrane" Science vol. 295 Jan. 4, 2002 pp. 105-107.
Peng, et al. "Highly selective and green aqueous-ionic liquid biphasic hydroxylation of benzene to phenol with hydrogen peroxide". Green Chemistry , 2003, 5, 224-226.
CN1385410. Publication Date Dec. 18, 2002. Method for preparing phenol by directly hydrocylating benzene. (Abstract only).
Xiao, et al. Synthesis and Structure of Copper Hydroxyphosphate and its High Catalytic Activity in Hydroxylation of Phenol by H202. Journal of Catalysis 199, 273-281 (2001).
International Search Report for International Application No. PCT/US2005/026622, mailed Jun. 28, 2006.
Lissel et al. "Oxidation of Activated Phenois by Dioxygen Catalysed by the H5PV2Mo10O40 Heteropolyanion" Tetrahedron Letters, vol. 33, No. 13, 1992, pp. 1795-1798.
Mal et al. "Synthesis of hexagonal and cubic super-microporous niobium phosphates with anion exchange capacity and catalytic properties" Chem. Comm. Oct. 2002, pp. 2702-2703.
Matveev et al. "Phase-transfer oxidation of 2-methyl-1-naphthol into 2-methyl-1, 4-naphthoquinone in the presence of vanadomolybdophosphoric heteropolyacids" Russian Chemical Bulletin, vol, 43, No. 7, Jul. 1994, pp. 1142-1145.
Shimizu et al. "A Convenient Synthesis of Alkyl-Substituted p-Benzoquinones From Phenols by a H202/Heteropolyacid System" Tetrahedron Letters, vol. 30, No. 4, 1989, pp. 471-474.
Villemin et al. "Supported Metalated Phthalocyanine as Catalyst for Oxidation by Molecular Oxygen, Synthesis of Quinones and Carbonyl Compounds" Synthetic Communications, vol. 32, No. 10, 2002, pp. 1501-1515.

* cited by examiner

*Primary Examiner*—Sikarl A. Witherspoon

(57) ABSTRACT

A process for the preparation of hydroquinone compounds comprising, reacting an aromatic hydroxy compound with an oxidizing agent in a biphasic solvent system. The reaction is carried out in the presence of a transition metal hydroxy phosphate catalyst to produce the corresponding hydroquinone compound.

23 Claims, No Drawings

PROCESSES FOR PREPARING BENZOQUINONES AND HYDROQUINONES

BACKGROUND

This disclosure generally relates to a process for preparing hydroquinone compounds from aromatic hydroxy compounds.

Hydroquinone compounds find applications in a wide range of industries including, among others, the polymer industry, the dye industry, and the photographic industry as well as in medical applications. They are also known for fabricating polycarbonates for use in liquid crystal displays.

Oxidation of phenol with hydrogen peroxide in the presence of a catalyst to produce dihydric phenol has been studied using a variety of catalysts systems including strong acids and zeolites. However reactions using these catalysts yield mostly ortho dihydric phenols (catechols) with decreased selectivity for para dihydric phenol (hydroquinone) and its derivatives.

A number of attempts have been made to improve reaction selectivity for hydroquinones over catechols in a variety of catalyst systems. However each approach suffers one or more significant drawbacks such as difficulty in separating the catalyst from the product, catalyst cost and environmental concerns regarding one or more components of the reaction system. These drawbacks make these approaches commercially undesirable.

Accordingly, there is a need in the art for a commercial and cost effective process for manufacturing dihydric phenols with improved para selectivity.

BRIEF SUMMARY

Disclosed herein is a process for the preparation of hydroquinone compounds. The process comprises reacting an aromatic hydroxy compound with an oxidizing agent in a biphasic solvent system. The reaction is carried out in the presence of a transition metal hydroxy phosphate catalyst to produce the corresponding hydroquinone compound.

The disclosure may be understood more readily by reference to the following detailed description of the various features of the disclosure and the examples included therein.

DETAILED DESCRIPTION

Disclosed herein is a process for preparing hydroquinone compounds that is cost effective and has high conversion and high selectivity. The process comprises reacting an aromatic hydroxy compound with an oxidizing agent in a biphasic solvent system in the presence of a transition metal hydroxy phosphate catalyst. The reaction produces the corresponding hydroquinone compound. The reaction may also produce the corresponding benzoquinone compound. The benzoquinone compound may be reduced to the hydroquinone compound.

Without being bound by theory, it is believed that the use of a biphasic solvent system partitions the starting aromatic hydroxy compound and the product benzoquinone and hydroquinone in a manner so as to result in a high degree of para selectivity. The benzoquinone compound may be reduced with a reducing agent to provide the corresponding hydroquinone compound thus improving the overall selectivity of the process.

The singular forms "a", "an" and "the" include plural referents unless the context clearly dictates otherwise. All ranges disclosed herein are inclusive and combinable (e.g., ranges of "up to 25 wt %, with 5 wt % to 20 wt % desired," is inclusive of the endpoints and all intermediate values of the ranges of "5 wt % to 25 wt %," etc.).

The hydroquinone compounds are prepared from aromatic hydroxy compounds of the formula:

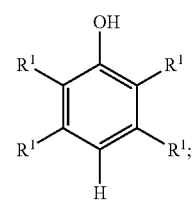

wherein each occurrence of $R^1$ is independently selected from the group consisting of a hydrogen and a hydrocarbyl group. The hydrocarbyl group may be selected from the group consisting of an alkyl group containing 1 to 18 carbon atoms, an aryl group containing 6 to 20 carbon atoms and an aralkyl group containing 6 to 12 carbon atoms.

Examples of aromatic hydroxy compounds include, but are not limited to, phenol, 2,6-dimethyl phenol, 2,6-di-tertiary-butyl phenol, 2-tertiary-butyl phenol, alpha-naphthol, meta-cresol, ortho-cresol, ortho-phenylphenol, ortho-benzylphenol, 2,3,6-trimethyl phenol, ortho-vinylphenol, 2-isopropylphenol, 2,6-diisopropylphenol, 2,3,5,6-tetramethylphenol, 2,3,5-trimethylphenol and mixtures of the foregoing aromatic hydroxy compounds. In one embodiment, the aromatic hydroxy compound is ortho-cresol.

Unless otherwise specified, the term "alkyl" as used herein is intended to designate straight chain alkyls and branched chain alkyl groups. Illustrative non-limiting examples of suitable straight chain and branched chain alkyl groups include methyl, ethyl, n-propyl, isopropyl, n-butyl, sec-butyl, tertiary-butyl, pentyl, neopentyl, hexyl, heptyl, octyl, nonyl, decyl, undecyl and dodecyl. Aralkyl groups include, but are not intended to be limited to, benzyl, phenylbutyl, phenylpropyl, and phenylethyl. In various other embodiments, the term "aryl" or "aromatic" groups are intended to designate monocyclic or polycyclic moieties containing 6 to 20 ring carbon atoms. Some illustrative non-limiting examples of these aromatic groups include phenyl, biphenyl, and naphthyl.

The oxidation is carried out using an oxidizing agent selected from the group consisting of, but not intended to be limited to, hydrogen peroxide, cumene hydroperoxide, tertiary-butyl hydroperoxide and peracetic acid. In one embodiment, the oxidation is carried out using hydrogen peroxide. The amount of hydrogen peroxide used is 0.1 moles to 1.1 moles per mole of aromatic hydroxy compound, or, more specifically 0.2 moles to 0.5 moles, or, even more specifically, 0.3 moles to 0.4 moles. Use of hydrogen peroxide in an amount greater than 0.33 moles per mole of aromatic hydroxy compound may lead to a decrease in selectivity. Hydrogen peroxide is available commercially as a 30% weight by volume solution in water. The rate at which hydrogen peroxide is added to the reaction mixture comprising water, hydroxy aromatic compound and solvent is 5 milliliters per hour to 50 milliliters per hour, or more specifically 10 milliliters per hour to 40 milliliters per hour, or, even more specifically, 15 milliliters per hour to 35 milliliters per hour. The amount of other oxidizing agents as well as their rate of addition, if different from hydrogen peroxide, can be readily determined by one of ordinary skill in the art based upon the information provided for hydrogen peroxide.

The transition metal hydroxy phosphate catalyst comprises at least one transition metal capable of forming a hydroxy phosphate that is stable in the presence of water and oxygen. The transition metal hydroxy phosphate may be selected from the group consisting of, but not limited to, copper hydroxy phosphate, manganese hydroxy phosphate, copper-manganese hydroxy phosphate, iron hydroxy phosphate, nickel hydroxy phosphate and mixtures of the foregoing hydroxy phosphates. More particularly, the oxidation may be carried out using copper hydroxy phosphate, manganese hydroxy phosphate or copper-manganese hydroxy phosphate. In one embodiment the transition metal hydroxy phosphate employed is copper hydroxy phosphate.

The transition metal hydroxy phosphates can be prepared by known procedures, for example by following the methods described in Journal of Catalysis 199, 273–281 (2001). In an exemplary procedure a transition metal compound such as a metal acetate is reacted in water with phosphoric acid and a diamine such as ethylene diamine. The resulting product, typically a gel or other solid, is heated to obtain a crystalline or semi-crystalline material, typically at a temperature of 140° C. to 160° C. for 1 to 4 days.

The amount of the transition metal hydroxy phosphate catalyst employed is 0.05 to 10 weight percent, or, more specifically 0.1 to 8 weight percent, or, even more specifically 0.2 to 5 weight percent, based on the weight of the aromatic hydroxy compound.

The oxidation of the aromatic hydroxy compound with the oxidizing agent is carried out in a biphasic solvent system comprising water and water-immiscible solvent. Water-immiscible solvents are generally those solvents which when allowed to stand and remain undisturbed, after being initially mixed with water, separate out into a distinct layer different from the water layer. The two layers (or phases) are visible to the naked eye. The water-immiscible solvent may be selected from the group consisting of aliphatic straight chain, branched chain or cyclic solvents having 6 to 15 carbon atoms or mixtures of two of more of the foregoing solvents. Exemplary water-immiscible solvents include, but are not limited to, cyclohexane, n-heptane, hexane, octanol, n-decane, decalene and mixtures of two or more of the foregoing solvents. The amount of water-immiscible solvent used in the oxidation reaction is 10 milliliters to 1000 milliliters per mole of aromatic hydroxy compound. Within this range the amount of water-immiscible solvent used is 100 milliliters to 800 milliliters, or, more specifically 200 to 600 milliliters, or, even more specifically 300 milliliters to 400 milliliters water-immiscible solvent per mole of aromatic hydroxy compound.

Advantageously, the use of a biphasic solvent system comprising water and water-immiscible solvent increases the peroxide efficiency and simultaneously provides better para selectivity as indicated by higher formation of benzoquinone compound and hydroquinone compound when compared to ortho dihydric phenols and tars. The peroxide efficiency can be calculated as given below.

Peroxide efficiency=(number of moles of hydroquinone formed×100/number of moles of hydrogen peroxide converted)+(number of moles of benzoquinone formed×100/number of moles of hydrogen peroxide converted).

The hydroquinone compound is substantially free of metal derived from the transition metal hydroxy phosphate catalyst. Substantially free, as used herein, may be defined as containing less than or equal to 1000 parts per million (ppm) metal from the transition metal hydroxy phosphate catalyst, or, more specifically, less than or equal to 800 ppm, or, even more specifically, less than or equal to 500 ppm.

The oxidation of the aromatic hydroxy compound with the oxidizing agent may be carried out at a temperature sufficiently low to prevent substantial decomposition of the oxidizing agent employed. This is to ensure maximum efficiency of the oxidizing agent. Typically when hydrogen peroxide is employed as the oxidizing agent the reaction temperature is 25° C. to 80° C., or more specifically, the temperature is 65° C. to 75° C., or, even more specifically the temperature is 60° C. to 75° C.

The time required for the oxidation is 1 hour to 24 hours, or more specifically is 2 hours to about 10 hours, or even more specifically 2 hours to 6 hours. The oxidation of the aromatic hydroxy compound in presence of the catalyst is typically carried out at atmospheric pressure although alternate pressures may be employed depending upon the choice of solvents, reactants and products. The formation of oxidation products may be monitored by using high performance liquid chromatography (HPLC) techniques.

The process described hereinabove can be conducted either in a batch process, semi-continuous process or continuous process. The batch reaction generally proceeds through the addition of the oxidizing agent to a mixture of water, aromatic hydroxy compound and solvent contained in a reactor with the catalyst. In the continuous mode a stream of oxidizing agent and another stream comprising water, aromatic hydroxy compound and solvent can be simultaneously passed over the catalyst contained in a fixed bed or fluidized bed reactor.

Presence of water in the reaction mixture facilitates the para-selectivity of the oxidation reaction. The amount of water required is enough to maintain a biphasic system. Without being bound by theory, use of a biphasic system i.e. partitioning, at least in part, the reactant and catalyst from the products, assists in reduced formation of products with more than two hydroxyl groups. The hydroquinone and benzoquinone products formed are believed to have greater affinity for the non-aqueous phase than the starting aromatic hydroxy compound and hence migrate into the non-aqueous phase once they are formed. As a result the aromatic hydroxy compound present in the non-aqueous phase goes into the aqueous phase and gets subsequently oxidized. The amount of water used is 100 milliliters to 2000 milliliters per mole of the aromatic hydroxy compound. Within this range the amount of water used may be 200 milliliters to 1500 milliliters, or, more specifically 300 milliliters to 900 milliliters or, even more specifically, 400 milliliters to 600 milliliters per mole of the aromatic hydroxy compound.

Optionally, the mixture comprising benzoquinone compound and hydroquinone compound present in the water-immiscible solvent may be subjected to reducing conditions to convert the benzoquinone to hydroquinone. The water-immiscible solvent used in the oxidation reaction is compatible for reduction and hence the organic phase (non-aqueous phase) can directly be taken for reduction. Exemplary reducing agents include hydrogen gas or hydrogen gas containing mixtures in presence of a reduction catalyst or the reducing agent. Exemplary reducing agents include sodium borohydride, sodium dithionate, lithium aluminum hydride, sodium hydrosulfite and sodium bisulfite. Exemplary reduction catalysts include Raney nickel, palladium-carbon, palladium supported on alumina, palladium supported on silica, platinum supported on charcoal, platinum supported on alumina, platinum supported on silica, platinum supported on silica-alumina, palladium supported on silica-alumina, tin, iron-hydrochloric acid, and zinc-acetic acid. It is desirable for reduction conditions to be chosen so as to reduce the benzoquinone with little or no reduction of the hydroquinone in the mixture.

The oxidation reaction as described above has a peroxide efficiency of greater than or equal to 35%. Within this range the peroxide efficiency may be greater than or equal to 40%, or, more specifically, greater than or equal to 45%, or, even more specifically, greater than or equal to 50%. The oxidation reaction also has a para-selectivity greater than or equal to 25%. Within this range the para-selectivity may be greater than or equal to 35%, or, more specifically, greater than or equal to 45% or, even more specifically, greater than or equal to 50%. Para-selectivity is determined by the amount of aromatic hydroxy compound being converted into corresponding hydroquinone and benzoquinone products.

As previously discussed, the hydroquinone compounds find various end use applications in the polymer, dyestuff, pharmaceutical and photographic industries as well as in medical applications. Polycarbonates containing repeating units derived from methyl hydroquinone are known to exhibit liquid crystalline properties. These polycarbonates may be prepared by reacting a carboxylate precursor, such a phosgene or a diaryl carbonate, with one or more hydroquinones or a mixture of one or more hydroquinones and a dihydroxy aromatic compound such as a bisphenol. The hydroquinone compounds may also be used to prepare polyesters when coupled with other monomers by melt polymerization techniques as is known in the art. Further, since the hydroquinone compounds are substantially free of metal derived from the catalyst, this may avoid the free radical and oxidation reactions that could occur during subsequent polymerization reactions that employ the hydroquinone as a monomer. This may prevent the formation of quinone and metal-quinone type colored molecules which can color the polycarbonate. The polycarbonate is substantially free of metal derived from the transition metal hydroxy phosphate catalyst.

The disclosure is explained in more detail with reference to the following non-limiting Examples.

EXAMPLES

In the following examples and comparative examples, a high performance liquid chromatography (HPLC) method was used to quantify the conversion of o-cresol to a mixture comprising the corresponding benzoquinone and hydroquinone compounds. The HPLC was initially calibrated using standard Aldrich samples of o-cresol and the corresponding hydroquinone and benzoquinone diluted with an internal standard solution of N-methyl benzamide in acetonitrile. The diluted standard samples were injected into a C-18 reverse phase column. A sample of the reaction mixture was made homogenous by the addition of a water miscible solvent e.g. acetonitrile or acetone. The reaction mixture sample was then diluted with an internal standard solution of N-methyl benzamide in acetonitrile and injected into a C-18 reverse phase column. Samples at specific time intervals were analyzed and compared to the HPLC chromatogram of the standard sample to determine the conversion of aromatic hydroxy compound and selectivity towards corresponding benzoquinone and hydroquinone. At the end of the peroxide addition, the reaction mixture was made homogeneous by the addition of a water miscible solvent and analyzed by HPLC. The conversion of o-cresol was determined by estimating the amount of o-cresol present in the reaction mixture at the end of the reaction by HPLC and deducting it from the amount of o-cresol added to the reaction. The selectivity towards benzoquinone and hydroquinone were calculated as:

Percentage selectivity of aromatic hydroxy compound conversion towards hydroquinone $$(S1) = \frac{\text{Number of moles of hydroquinone formed} \times 100}{\text{Number of moles of aromatic hydroxy compound converted}}$$

Percentage selectivity of aromatic hydroxy compound towards benzoquinone $$(S2) = \frac{\text{Number of moles of benzoquinone formed} \times 100}{\text{Number of moles of aromatic hydroxy compound converted}}$$

The combined selectivity (S) towards benzoquinone and hydroquinone is S=S1+S2

Example 1

In this example, copper hydroxy phosphate was prepared hydrothermally using ethylene diamine, phosphoric acid and copper acetate as starting materials. The molar ratio of the reactants used were ethylene diamine (1.0 mole): phosphoric acid (2.9 moles): copper acetate(1.0 mole): water (25 moles). Copper acetate was added to the water with stirring and the stirring maintained for 30 minutes, followed by the addition of phosphoric acid. The mixture was stirred for 1.5 hours after the addition of the phosphoric acid and then ethylene diamine was added, and the pH was maintained between 2 and 5. The mixture was then stirred to obtain a homogenous gel. The gel was sealed in a Teflon-lined stainless steel autoclave and heated for 3 days at 150° C. The resulting crystalline product was filtered, washed with distilled water, and dried at ambient temperature. Manganese hydroxy phosphate was prepared in a similar manner by substituting manganese acetate for copper acetate. The copper-manganese hydroxy phosphate was also prepared accordingly by replacing copper acetate with a mixture of copper acetate and manganese acetate in a 1:1 mole ratio. All these samples were characterized by X-ray diffraction (XRD). X-ray diffraction results are comparable to the values reported in the Journal of Catalysis 199, 273–281 (2001), and confirm synthesis of the desired metal hydroxy phosphate. The 2 theta values and corresponding intensities for copper hydroxy phosphate are included in Table I.

TABLE I

XRD characterization of copper hydroxy phosphate.

| | 2 theta | | | | | | |
|---|---|---|---|---|---|---|---|
| | 15.37 | 18.45 | 30.89 | 34.17 | 35.11 | 39.09 | 53.67 | 58.31 |
| Intensity | 12 | 100 | 4 | 6 | 6 | 5 | 11 | 7 |

Example 2–4

General procedure followed for the preparation of a mixture comprising benzoquinone and hydroquinone from ortho-cresol is set forth below. Hydrogen peroxide (30 weight percent) was added to a mixture of water, water-immiscible solvent, catalyst and ortho-cresol at a specific rate. The amount of water, water-immiscible solvent, catalyst, ortho-cresol, hydrogen peroxide (30 weight percent) and the reaction parameters including temperature and rate of hydrogen peroxide addition are set forth in Table II below. The conversion of ortho-cresol, peroxide efficiency and quantity of benzoquinone and hydroquinone are included in Table III.

It is observed that the peroxide efficiency and the combined para selectivity towards formation of methyl hydroquinone and methyl benzoquinone from ortho-cresol, is greater than double when a biphasic solvent system is used in Example 1 as compared to a single solvent used in Comparative Example 1.

While the invention has been described with reference to an exemplary embodiment, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims.

The invention claimed is:

1. A process comprising:
   oxidizing an aromatic hydroxy compound with an oxidizing agent in a biphasic solvent system in the presence of a transition metal hydroxy phosphate catalyst to produce a corresponding hydroquinone compound;
   wherein the aromatic hydroxy compound has a formula:

TABLE II

| Example | o-Cresol gm | Catalyst | $H_2O_2$ (30% wt./Vol), ml | $H_2O_2$ addition rate, ml/hr | Catalyst loading with respect to o-cresol, wt. % | Temperature, °C. | Time. Hrs | Water (ml) | Water-immiscible solvent (ml) |
|---|---|---|---|---|---|---|---|---|---|
| 1 | 3.84 | $Cu_2(OH)PO4$ | 1.22 | 0.61 | 5 | 66 | 2 | 20 | Cyclohexane (12.8) |
| 2 | 3.85 | $Cu_2(OH)PO4$ | 1.22 | 0.61 | 0.25 | 73 | 2 | 20 | n-Heptane (29.4) |
| 3 | 2.88 | $Cu_2(OH)PO4$ | 0.92 | 0.4 | 5 | 73 | 2.3 | 15 | n-Decane(10.3) |
| 1* | 3.84 | $Cu_2(OH)PO_4$ | 1.22 | 0.61 | 5 | 66 | 2 | 30 | 0 |
| 2* | 3.85 | $Cu_2(OH)PO_4$ | 1.22 | 0.61 | 5 | 73 | 2 | 30 | 0 |
| 3* | 1.95 | $Cu_2(OH)PO_4$ | 0.61 | 0.61 | 5 | 73 | 1 | 0 | Acetonitrile (15) |

*indicates comparative examples

TABLE III

| Example | o-Cresol Conversion, % | Selectivity towards MeHQ, % | Selectivity to MeBQ, % | Combined para selectivity, % | Selectivity to MeCat, % | H2O2 Conversion, % | Peroxide efficiency towards MeHQ and MeBQ, % |
|---|---|---|---|---|---|---|---|
| 1 | 23.41 | 25.7 | 31.3 | 57 | 0 | 71.6 | 57.85 |
| 2 | 28.63 | 16.7 | 21.6 | 38.3 | 0 | 69.75 | 48.73 |
| 3 | 30.27 | 2.78 | 23.91 | 26.69 | 0 | 71.6 | 34.82 |
| 1* | 24.02 | 0 | 22.64 | 22.64 | 6.24 | 65.6 | 27.4 |
| 2* | 29.9 | 0 | 16.77 | 16.77 | 5.48 | 77 | 21.5 |
| 3* | 2.36 | 0 | 31.66 | 31.66 | 0 | 33.43 | 2.23 |

*indicates comparative examples

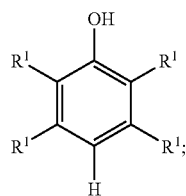

wherein each occurrence of $R^1$ is independently selected from the group consisting of a hydrogen and a hydrocarbyl group.

2. The process of claim 1, wherein said hydroquinone compound is mixed with a corresponding benzoquinone compound.

3. The process of claim 1, wherein said aromatic hydroxy compound is selected from the group consisting of phenol, 2,6-dimethyl phenol, 2,6-di-tertiary-butyl phenol, 2-tertiary-butyl phenol, alpha-naphthol, meta-cresol, ortho-cresol, ortho-phenylphenol, ortho-benzylphenol, 2,3,6-trimethyl phenol, ortho-vinylphenol, 2-isopropylphenol, 2,6-diisopropylphenol, 2,3,5,6-tetramethylphenol, 2,3,5-trimethylphenol, and mixtures of two or more of the foregoing aromatic hydroxy compounds.

4. The process of claim 1, wherein said aromatic hydroxy compound comprises ortho-cresol.

5. The process of claim 1, wherein said oxidizing agent is selected from the group consisting of hydrogen peroxide, cumene hydroperoxide, tertiary-butyl hydroperoxide and peracetic acid.

6. The process of claim 1, wherein said oxidizing agent is hydrogen peroxide.

7. The process of claim 1, wherein said transition metal hydroxy phosphate is selected from the group consisting of copper hydroxy phosphate, manganese hydroxy phosphate, copper-manganese hydroxy phosphate, iron hydroxy phosphate and nickel hydroxy phosphate.

8. The process of claim 1, wherein the amount of said transition metal hydroxy phosphate catalyst is 0.05 to 10 weight percent based on the weight of the aromatic hydroxy compound.

9. The process of claim 1, wherein said reaction occurs at a temperature of 25° C. to 80° C.

10. The process of claim 1, wherein the biphasic solvent system comprises water and a water-immiscible solvent.

11. The process of claim 10, wherein the water-immiscible solvent is selected from aliphatic straight chain, branched chain or cyclic solvents having 6 to 15 carbon atoms or mixtures of two of more of the foregoing solvents.

12. The process of claim 10, the water-immiscible solvent is selected from the group consisting of cyclohexane, n-heptane, hexane, octanol, n-decane and decalene.

13. The process of claim 1, wherein the amount of water-immiscible solvent used is 10 milliliters to 1000 milliliters per mole of the aromatic hydroxy compound.

14. The process of claim 1, wherein the amount of water used is 100 milliliters to 2000 milliliters per mole of the aromatic hydroxy compound.

15. The process of claim 1, wherein said process is carried out in a batch mode, semi-continuous mode or in a continuous mode.

16. The process of claim 15, wherein said batch mode is carried out for 1 to 24 hours.

17. The process of claim 1, wherein said hydroquinone is substantially free of metal derived from the transition metal hydroxy phosphate catalyst.

18. A method of making a polycarbonate comprising reacting a carboxylate precursor and one or more hydroquinones or a mixture of one or more hydroquinones and a dihydroxy aromatic compound wherein the one or more hydroquinones is prepared according to the process of claim 1.

19. A process for preparing 2-methylhydroquinone, said process comprising:
reacting ortho-cresol with hydrogen peroxide in a biphasic solvent system in the presence of a transition metal hydroxy phosphate catalyst to form said hydroquinone compound, wherein the biphasic system comprises a mixture of water and water-immiscible solvent and wherein the transition metal hydroxy phosphate catalyst is selected from a group consisting of a copper hydroxy phosphate, manganese hydroxy phosphate and a copper manganese hydroxy phosphate.

20. The process of claim 19, wherein said 2-methyl hydroquinone compound is substantially free of metal derived the from the transition metal hydroxy phosphate catalyst.

21. The process of claim 19, wherein said 2-methylhydroquinone compound is mixed with a corresponding benzoquinone compound.

22. The process of claim 19, the water-immiscible solvent is selected from the group consisting of cyclohexane, n-heptane, hexane, octanol, n-decane and decalene.

23. A method of making a polycarbonate comprising reacting a carboxylate precursor and a one or more hydroquinones or a mixture of one or more hydroquinones and a dihydroxy aromatic compound wherein the one or more hydroquinones is prepared according to claim 19.

* * * * *